(12) United States Patent
Yribarren (10) Patent No.: US 8,685,047 B2
(45) Date of Patent: Apr. 1, 2014

(54) SCAFFOLD DEVICE FOR PREVENTING TISSUE TRAUMA

(75) Inventor: Travis R. Yribarren, Campbell, CA (US)

(73) Assignee: Abbott Vascular, Inc., Santa Clara, CA (US)

(*) Notice: Subject to any disclaimer, the term of this patent is extended or adjusted under 35 U.S.C. 154(b) by 0 days.

(21) Appl. No.: 13/022,246

(22) Filed: Feb. 7, 2011

(65) Prior Publication Data
US 2012/0203328 A1 Aug. 9, 2012

(51) Int. Cl.
*A61B 17/08* (2006.01)

(52) U.S. Cl.
USPC .................. 606/153; 623/1.18; 606/155

(58) Field of Classification Search
USPC .............. 623/1.15, 1.36, 1.18; 606/213, 606/215–217, 151, 232
See application file for complete search history.

(56) References Cited

U.S. PATENT DOCUMENTS

| | | | |
|---|---|---|---|
| 2,449,235 A | 9/1948 | Krupp | |
| 3,766,610 A | 10/1973 | Thorsbakken | |
| 4,156,574 A | 5/1979 | Boden | |
| 4,807,333 A | 2/1989 | Boden | |
| 5,292,332 A | 3/1994 | Lee | |
| 5,342,393 A | 8/1994 | Stack | |
| 5,417,699 A | 5/1995 | Klein et al. | |
| 5,435,044 A | 7/1995 | Ida | |
| 5,454,140 A | 10/1995 | Murai | |
| 5,478,353 A | 12/1995 | Yoon | |
| 5,520,070 A | 5/1996 | Beugelsdyk et al. | |
| 5,520,702 A | 5/1996 | Sauer et al. | |
| 5,562,689 A | 10/1996 | Green et al. | |
| 5,569,306 A | 10/1996 | Thai | |
| 5,572,770 A | 11/1996 | Boden | |
| 5,630,824 A | 5/1997 | Hart | |
| 5,658,313 A | 8/1997 | Thal | |
| 5,702,397 A | 12/1997 | Goble et al. | |
| 5,725,529 A | 3/1998 | Nicholson et al. | |
| 5,779,707 A * | 7/1998 | Bertholet et al. | 606/75 |
| 5,893,856 A | 4/1999 | Jacob et al. | |
| 5,902,311 A | 5/1999 | Andreas et al. | |
| 5,941,901 A | 8/1999 | Egan | |
| 5,584,861 A | 7/2000 | Ek et al. | |
| 6,086,608 A | 7/2000 | Ek et al. | |
| 6,099,547 A | 8/2000 | Gellman et al. | |
| 6,136,010 A | 10/2000 | Modesitt et al. | |

(Continued)

FOREIGN PATENT DOCUMENTS

| | | |
|---|---|---|
| WO | WO 02/15795 | 2/2002 |
| WO | WO 2005/027754 | 3/2005 |

OTHER PUBLICATIONS

U.S. Appl. No. 12/917,195, filed Nov. 1, 2010, Voss et al.
U.S. Appl. No. 13/035,939, filed Feb. 26, 2011, Ehrenreich.

(Continued)

*Primary Examiner* — David H. Willse
*Assistant Examiner* — Tiffany Shipmon
(74) *Attorney, Agent, or Firm* — Workman Nydegger; Randy Shen (57) ABSTRACT

A scaffold is provided for managing access through tissue. The scaffold can support the tissue during medical procedures. The scaffold is placed around or proximate an opening in tissue. The scaffold can expand when medical devices are introduced through the scaffold and through the opening and retract when the medical devices are removed. When the medical devices are removed, the scaffold closes automatically to substantially close the opening.

32 Claims, 4 Drawing Sheets

(56) References Cited

U.S. PATENT DOCUMENTS

| | | |
|---|---|---|
| 6,200,329 B1 | 3/2001 | Fung et al. |
| 6,206,895 B1 | 3/2001 | Levinson |
| 6,231,592 B1 | 5/2001 | Bonutti et al. |
| 6,245,080 B1 | 6/2001 | Levinson |
| 6,277,140 B2 | 8/2001 | Ginn et al. |
| 6,398,796 B2 | 6/2002 | Levinson |
| 7,011,400 B2 | 3/2006 | Nakano |
| 7,662,161 B2 | 2/2010 | Briganti et al. |
| 7,713,284 B2 | 5/2010 | Crofford |
| 7,947,062 B2 | 5/2011 | Chin et al. |
| 8,100,923 B2 | 1/2012 | Paraschac et al. |
| 8,128,653 B2 | 3/2012 | McGuckin, Jr. et al. |
| 2001/0044638 A1 | 11/2001 | Levinson et al. |
| 2001/0044639 A1 | 11/2001 | Levinson |
| 2002/0002401 A1* | 1/2002 | McGuckin et al. .......... 623/1.19 |
| 2002/0077658 A1 | 6/2002 | Ginn |
| 2002/0082641 A1 | 6/2002 | Ginn et al. |
| 2002/0107542 A1* | 8/2002 | Kanner et al. ................ 606/213 |
| 2002/0151921 A1 | 10/2002 | Kanner et al. |
| 2002/0169478 A1 | 11/2002 | Schwartz et al. |
| 2002/0188318 A1 | 12/2002 | Carley et al. |
| 2003/0093096 A1 | 5/2003 | McGuckin, Jr. et al. |
| 2003/0144695 A1 | 7/2003 | McGuckin, Jr. et al. |
| 2003/0167062 A1 | 9/2003 | Gamabale et al. |
| 2003/0195514 A1 | 10/2003 | Trieu et al. |
| 2003/0199987 A1* | 10/2003 | Berg et al. .................. 623/23.64 |
| 2004/0093024 A1* | 5/2004 | Lousararian et al. ......... 606/213 |
| 2004/0158309 A1 | 8/2004 | Wachter et al. |
| 2005/0038500 A1 | 2/2005 | Boylan et al. |
| 2005/0205640 A1 | 9/2005 | Milliman |
| 2006/0190037 A1 | 8/2006 | Ginn et al. |
| 2006/0235505 A1* | 10/2006 | Oepen et al. ................. 623/1.15 |
| 2006/0241579 A1 | 10/2006 | Kawaura et al. |
| 2006/0265008 A1 | 11/2006 | Maruyama et al. |
| 2006/0265010 A1 | 11/2006 | Paraschac et al. |
| 2007/0010853 A1 | 1/2007 | Ginn et al. |
| 2007/0255317 A1 | 11/2007 | Fanton et al. |
| 2007/0270904 A1 | 11/2007 | Ginn |
| 2007/0276433 A1 | 11/2007 | Huss |
| 2007/0276488 A1 | 11/2007 | Wachter et al. |
| 2008/0312740 A1 | 12/2008 | Wachter et al. |
| 2009/0157102 A1 | 6/2009 | Reynolds et al. |
| 2009/0306671 A1 | 12/2009 | McCormack et al. |
| 2010/0256670 A1 | 10/2010 | Ginn et al. |
| 2011/0029012 A1 | 2/2011 | Tegels |
| 2012/0184991 A1 | 7/2012 | Paraschac et al. |

OTHER PUBLICATIONS

U.S. Appl. No. 13/219,004, filed Aug. 26, 2011, Roorda.
U.S. Appl. No. 13/411,320, filed Mar. 3, 2012, Voss et al.
U.S. Appl. No. 12/684,470, filed Jan. 8, 2010, Voss et al.
U.S. Appl. No. 12/917,195, filed Jun. 28, 2012, Restriction Requirement.
U.S. Appl. No. 12/917,195, filed Aug. 1, 2012, Office Action.
U.S. Patent No. 60/502925, filed Sep. 15, 2003, Paraschac.
U.S. Appl. No. 10/941,693, filed Nov. 17, 2006, Office Action.
U.S. Appl. No. 10/941,693, filed May 7, 2007, Office Action.
U.S. Appl. No. 10/941,693, filed Dec. 31, 2007, Office Action.
U.S. Appl. No. 10/941,693, filed Jul. 9, 2008, Office Action.
U.S. Appl. No. 10/941,693, filed Mar. 2, 2009, Office Action.
U.S. Appl. No. 10/941,693, filed Oct. 23, 2009, Office Action.
U.S. Appl. No. 10/941,693, filed Sep. 28, 2011, Notice of Allowance.
U.S. Appl. No. 11/460,863, filed Jul. 12, 2007, Office Action.
U.S. Appl. No. 11/460,863, filed Feb. 5, 2008, Office Action.
U.S. Appl. No. 11/460,863, filed Oct. 10, 2008, Office Action.
U.S. Appl. No. 11/460,863, filed Apr. 13, 2009, Office Action.
U.S. Appl. No. 12/917,195, filed May 6, 2013, Office Action.
U.S. Appl. No. 13/035,939, filed Jan. 31, 2013, Office Action.
U.S. Appl. No. 13/219,004, filed Dec. 19, 2012, Restriction Requirement.
U.S. Appl. No. 13/219,004, filed Feb. 14, 2013, Office Action.
U.S. Appl. No. 12/917,195, filed Aug. 7, 2013, Notice of Allowance.
U.S. Appl. No. 13/219,004, filed Aug. 9, 2013, Office Action.
U.S. Appl. No. 14/052,658, filed Oct. 11, 2013, Ehrenreich.
U.S. Appl. No. 13/035,939, filed Sep. 10, 2013, Office Action.

* cited by examiner

SCAFFOLD DEVICE FOR PREVENTING TISSUE TRAUMA

BACKGROUND

1. The Field of the Invention

Embodiments of the invention relate generally to medical devices. More particularly, embodiments of the invention relate to medical devices for managing access in body tissue.

2. The Relevant Technology

Catheterization and interventional procedures, such as angioplasty or stenting, are generally performed by inserting a hollow needle through a patient's skin and tissue into the patient's vascular system. A guide wire may be advanced through the needle and into the patient's vascular system. The needle is then removed leaving the guide wire in place, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. As the various devices are introduced through the introducer sheath, the opening or access site formed in the vessel may be subjected to additional trauma or tearing during the medical procedure.

Upon completing the procedure, the devices and introducer sheath are removed from the opening, leaving a puncture site or opening in the vessel wall. Traditionally, external pressure would be applied to the puncture site until clotting and wound sealing occur; however, the patient must remain bedridden for a substantial period after clotting to ensure closure of the wound. This procedure may be time consuming and expensive, requiring as much as an hour of a physician's or nurse's time. It is also uncomfortable for the patient and requires that the patient remain immobilized in the operating room, catheter lab, or holding area. In addition, the insertion and removal of various medical devices can lead to enlargement or tearing of the puncture site, which can complicate closure of the tissue opening.

BRIEF SUMMARY

Embodiments of the invention relate to a scaffold that provides tissue support. The scaffold is configured to be placed proximate an opening (e.g., an arteriotomy) in tissue. The scaffold engages the tissue to reduce or prevent trauma that the tissue experiences. During a medical procedure, for instance, the scaffold is configured to expand and contract. Expansion of the scaffold enables medical devices to be introduced through an interior area of the scaffold. The scaffold engages the tissue and can reduce or prevent trauma, for instance, from extending beyond the interior area of the scaffold.

In one example, the scaffold manages access to an opening in tissue and includes a body having a lower portion. The body includes an elastic material that can expand between first and second positions. The scaffold also includes anchors that extend from the lower portion and that are configured to engage the tissue proximate the opening.

In another example, the scaffold includes a body having an inner portion and an outer portion. The inner portion defines an interior area of the scaffold, and the body has a cross sectional area that changes when the body expands from a first position to a second position. The material also contracts from the second position to the first position. The scaffold also includes anchors extending from the body. The anchors narrow to a point and are configured to engage the tissue proximate the opening.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which at least some of the advantages and features of the invention can be obtained, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF EMBODIMENTS OF THE INVENTION

In general, embodiments of the invention relate to methods and devices for managing access to body lumens, for example by providing tissue support. Although various embodiments of the invention may be discussed with reference to a vessel, one of skill in the art can appreciate, with the benefit of the present disclosure, that embodiments of the invention can also be used in conjunction with other tissue, lumens, and/or with other procedures. More specifically, embodiments of the invention relate to a scaffold used in managing access to and/or through tissue and/or to body lumens.

In many medical procedures, it is often necessary to create an opening or an access site in tissue for various reasons, including to introduce medical devices into the tissue or into body lumens. For example, an opening is often formed in a vessel during a stenting procedure. After the opening is formed in the vessel, other medical devices are often introduced into the vessel lumen through the same opening. These medical devices are often larger than the needle that formed the opening. As a result, the opening is likely to be enlarged in order to accommodate those medical devices. In other words, the insertion, use, and/or removal of these medical devices may cause additional trauma to the vessel (e.g., tearing). In particular, the vessel wall proximate the opening is at risk of experiencing trauma.

Embodiments of the invention relate to a scaffold that may be placed around or proximate the opening formed in the vessel during these types of procedures. The scaffold is configured to reduce or minimize trauma to the vessel. For instance, the scaffold may reduce or minimize tearing that may occur at the opening during the insertion, use, and/or removal of medical devices such as an introducer sheath or for other reasons. Minimizing or reducing trauma to the vessel, by way of example only, can improve recovery time, keep the size of the opening to a minimum, and/or make the procedure easier to perform.

Generally, the scaffold is placed and anchored at a procedure site or in the tissue proximate the opening. The scaffold may be anchored at different locations around the opening. Anchoring the scaffold in the tissue proximate the opening enables the scaffold to retain the tissue and minimize tearing. By providing tissue support, the size of the opening can be constrained or minimized and tearing of the tissue is reduced or prevented. The scaffold can distribute and/or absorb forces experienced by the tissue during medical procedures. Often, any additional trauma experienced by the vessel may be limited by the scaffold.

The scaffold typically engages at least some of the tissue surrounding or proximate the opening in the tissue. Often the scaffold engages the tissue in various locations proximate the opening. Should a tear in the opening occur, the extent of the tear can be minimized by the scaffold. The scaffold may prevent the tear from expanding past the boundaries of the scaffold or keep the tearing within a certain area.

In order to allow the medical procedure to be performed or to control access to the opening in the tissue, the scaffold is configured to expand or stretch or deform. The change in the scaffold is often temporary and the scaffold will return to its original shape once the force is removed. The capability of the scaffold to alter its size and/or shape enables additional or larger medical devices to be introduced through the scaffold and through the opening in the vessel. The scaffold may have elastic elements that can stretch or temporarily adapt to the insertion, use, and/or removal of a medical device. The elasticity, flexibility, smoothness, and/or other aspects of the scaffold also enable the scaffold to accommodate movement of the medical device. The scaffold can dynamically adapt to changes in the orientation or position of the medical device while still providing tissue support.

When a medical device needs to be introduced through the opening in the vessel, the scaffold can be expanded or stretched to allow entry of the medical device. In this sense, the medical device is inserted through both the interior of the scaffold and the opening in the tissue in order to be introduced into the body lumen. Often, the medical device itself is able to expand the scaffold. In addition, the scaffold does not typically interfere with the insertion, removal, and/or use of the medical device.

When the medical device is removed, the scaffold may return to its original shape. In some examples, contraction of the scaffold may at least partially close the opening in the vessel. The scaffold, in this sense, can therefore provide tissue support and provide preclosure support as well.

The scaffold includes engagement mechanisms that can engage the vessel wall (or other tissue) proximate the opening. The engagement mechanisms anchor the scaffold to the vessel wall. The engagement mechanisms, for instance, may pierce or at least partially pierce the tissue proximate the opening to anchor the scaffold to the tissue. The engagement mechanisms remain anchored to the tissue (or vessel wall) during expansion and/or contraction of the scaffold.

When a medical device (e.g., an introducer sheath or catheter) needs to be introduced, the scaffold can be expanded to enable introduction of the medical device via the opening through the scaffold. When the medical device is withdrawn from the opening, the elasticity of the scaffold returns the scaffold to its previous shape, closing the opening in the vessel in some examples. Thus, the scaffold provides support and strength to the vessel to help the vessel withstand the medical procedure with reduced trauma.

Figure 1:
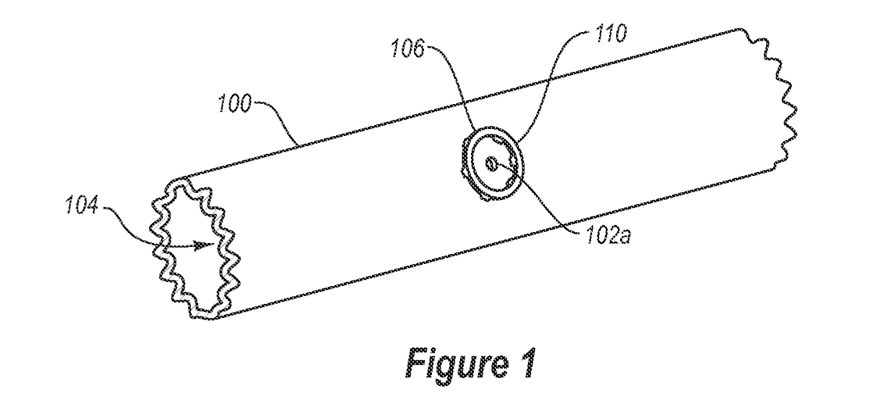
FIG. 1 shows a perspective view of a scaffold for managing access to a body lumen.
Figure 2:
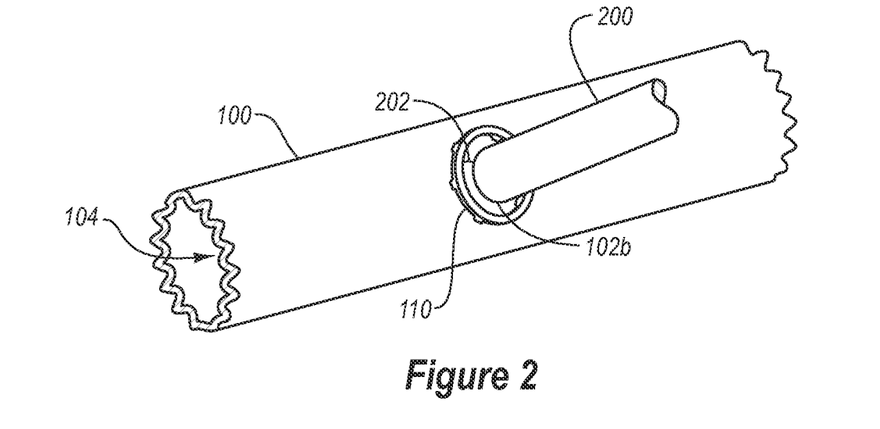
FIG. 2 shows a perspective view of the scaffold shown in FIG. 1 in an expanded position to accommodate the insertion of a medical device during a medical procedure.
Figure 3:
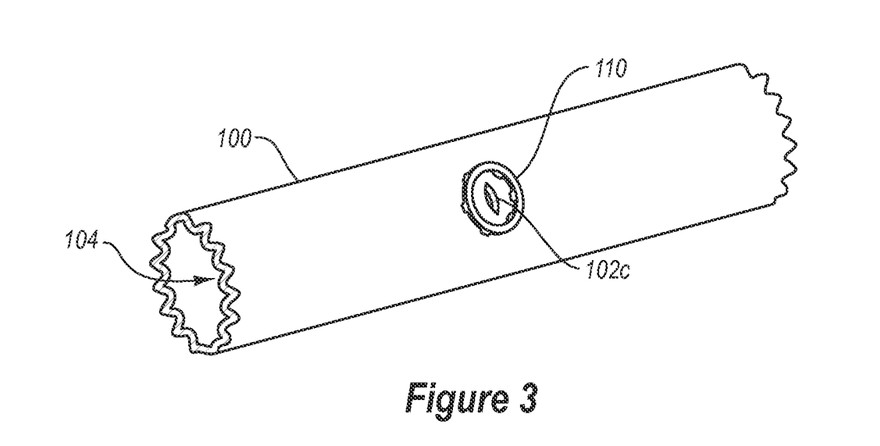
FIG. 3 shows a perspective view of the scaffold of FIG. 1 after removal of the medical device.

FIGS. 1-3 illustrate a scaffold 110 that provides tissue support during a medical procedure. The medical procedure is often performed through an opening 102 (illustrated as opening 102a, 102b, and 102c, respectively, in FIGS. 1, 2, and 3). The openings 102a, 102b, and 102c, illustrate the opening 102 before, during, and after the medical procedure in this example.

FIG. 1 shows an illustrative view of a scaffold 110 for providing tissue support, for example during a medical procedure. When performing the medical procedure, the medical procedure may include forming a puncture or opening 102a in a vessel 100. In FIG. 1, a wall 106 of the vessel 100 is punctured with a needle. The needle creates the opening 102a in the vessel and the needle is often used to insert a guide wire into a lumen 104 of the vessel 100. Once the needle is removed (leaving the guide wire in place in some instances), other medical devices can access the lumen 104 of the vessel 100 through the opening 102a.

Medical procedures, such as stenting procedures or the like, are often performed through the opening 102a in the vessel 100. As these procedures are performed, the necessary devices (e.g., an introducer sheath, catheter, etc.) are often introduced into the patient's vascular system through the opening 102a in the vessel 100.

In FIG. 1, the scaffold 110 has been placed at or proximate the opening 102a to provide, by way of example only, tissue support to the vessel 100. The scaffold 110 anchors in the vessel's wall 106 around or proximate the opening 102a to strengthen the area proximate the opening 102a and prevent or reduce trauma such as tearing at least within the area inside the boundaries of the scaffold 110. For instance, any tearing experienced at the opening 102a may be contained within the area inside the boundaries of the scaffold 110, which prevents the tear from extending beyond the boundaries of the scaffold 110.

The scaffold 110 can be placed on or anchored to the vessel 100 before, during, or after the opening 102 is formed in the vessel 100. However, a the scaffold 110 is typically positioned before other medical devices (e.g., an introducer sheath) are introduced through the opening 102a such that the scaffold 110 can minimize additional trauma (e.g., tearing) of the vessel 100 at the opening 102a. FIG. 1 shows the scaffold 110 in a contracted (at rest) or first position.

FIG. 1 also illustrates that the scaffold 110 may be shaped such that the opening 102a is closed or substantially closed when the scaffold 110 is initially deployed. Alternatively, the deployment of scaffold 110 may urge the partial closure of opening 102a. For example, the scaffold 110 may be partially expanded during deployment. As a result, the scaffold 110 contracts to gather or bunch the tissue inside the boundaries of the scaffold 110. In this manner, the scaffold 110 may be deployed such that the tissue within the boundaries of the scaffold 110 is bunched of slack compared to the vessel walls outside of the boundaries of the scaffold 110. For instance, the scaffold 110 may be slightly expanded prior to deployment. This can also aid in reducing trauma to the vessel during a procedure. Because the scaffold 110 is expandable or deformable, the scaffold 110 can deform to accommodate other medical devices and enable or control access through the opening 102.

FIG. 2 shows an illustrative example of the scaffold 110 during a medical procedure while controlling or managing access to the vessel 100 or to the lumen 104 of the vessel 100 through the opening 102b. FIG. 2 shows the scaffold 110 anchored or secured to the walls of the vessel 100 around or proximate the opening 102b. The scaffold 110 may be embedded in or fixed to the wall of the vessel 100 or have an engagement mechanism that can attach to the wall of the vessel 100. The attachment or connection between the scaffold 110 and the vessel 100 can be temporary and the scaffold 110 can be removed or repositioned if necessary. However, the scaffold 110 can remain anchored to the wall of the vessel 100 during the procedure or as long as necessary.

In some instances, the scaffold 110 may be formed from a biodegradable or biocompatible material. For example, portions of the scaffold 110 may be formed from a material selected from the group consisting of deformable metals, shape memory metals, ceramics, plastics, and shape memory plastics. Typically, the attachment or connection between the scaffold 110 and the vessel 100 is sufficiently strong to prevent displacement of the scaffold 110 during a medical procedure.

In FIG. 2, the scaffold 110 has been expanded or stretched by the insertion of a medical device 200, (e.g., an introducer sheath, a guiding catheter, or a balloon catheter). The device 200 is inserted through the interior of the scaffold 110 or within the boundaries of the scaffold 110 and then through the opening 102b into the lumen 104 of the vessel 100. The introduction of the device 200 may be used to expand the scaffold 200. Alternatively, another expanding device can be used to expand or stretch the scaffold 200 to enable introduction of the device 200. After the device 200 is introduced, the scaffold 110 contracts as permitted by the presence of the device 200. The elasticity and/or flexibility of the scaffold 110 enable the scaffold 110 to adapt dynamically to changes in the orientation and/or movement of the device 200. For instance, the scaffold 110 can change its position or its shape can adapt in accordance with at least distal, proximate, lateral, axial, and/or rotational movement of the device 200.

Because the device 200 is typically larger than the needle that initially formed the opening 102b, the larger size of the device 200 may cause the opening 102b to stretch or expand in order to accommodate insertion of the device 200. The scaffold 110 provides tissue support and may be able to control or at least limit the ultimate size of the opening 102b. For example, the scaffold 110 supports at least the tissue immediately around or proximate the opening 102b and may prevent tearing of the opening 102b during a medical procedure or during portions of the medical procedure (e.g., introduction of the device 200) and thus help reduce or minimize trauma at the opening 102b. In one example, the scaffold 110 distributes or absorbs forces that would otherwise tear the opening 102b to a larger area of the vessel 100, thus reducing the likelihood of additional trauma to the vessel 100.

FIG. 3 shows an illustrative example of the scaffold 110 after withdrawal of devices from the opening 102c in the vessel 100. Once the procedure is finished and the device 200 is removed, the scaffold 110 contracts or returns from an expanded or second position to its original shape or first position as illustrated in FIG. 3. When the scaffold 110 returns to its original, unstretched, unexpanded, or un-deformed state, the opening 102c may be closed or substantially closed by the scaffold 110. In one embodiment, the scaffold 110 may serve as a vessel closure device or preclosure device in addition to providing tissue support during the procedure. In this case, the opening 102c may not require any additional procedures that would otherwise be performed to close the opening 102c.

FIG. 3 illustrates that while the opening 102c after the procedure may be larger and or less smooth than when formed by the needle, the scaffold 110 reduces or minimizes trauma to the vessel 100. In this context, smoothness refers to the geometry of the opening being more angulated consistent with tissue tearing after insertion of a device as opposed to before. Further, the scaffold 110 can contract and bring the wall of the vessel 100 surrounding the opening 102c closer together to at least partially close the opening 102.

The size or dimensions of the scaffold 110 can vary. The scaffold 110 can be selected according to the medical devices that are being used for a given procedure. The scaffold 110 may also be selected according to properties of the material (e.g., rigidity, elasticity, deformability, smoothness, flexibility or the like or any combination thereof). The scaffold 110 should be selected such that when the scaffold 110 is fully expanded, the scaffold 110 can accommodate the necessary medical devices through the scaffold's interior. In some instances, the scaffold 110 may be able to expand to dimensions larger than the medical devices such that the scaffold 110 does not itself impede the introduction and/or removal of the various medical devices. FIG. 2, for example, illustrates a space 202 between the scaffold 110 and the device 200. However, the elasticity of the scaffold 110 may eliminate the space 202 such that the scaffold 110 is adjacent to or in contact with the device 200 during the procedure.

Figure 4:
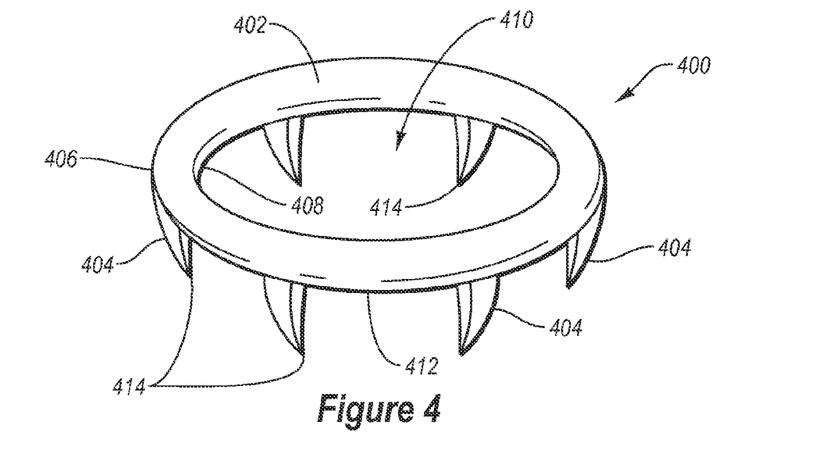
FIG. 4 shows a perspective view of a scaffold for reducing trauma to tissue.

FIG. 4 shows an illustrative embodiment of a scaffold 400, which is an example of the scaffold 110. The scaffold 400 includes a body 402. The body is typically formed of an elastic or at least partially elastic material that enables the scaffold 400 to be expanded in response to a force (e.g., insertion of a medical device) and to be contracted once the force is removed. During expansion of the scaffold 400, a size of an interior area 410 increases. The area 410 is an example of an area bounded by dimensions of the scaffold 400. In one example, the scaffold's body 402 is generally tubular and the cross section is generally circular. These shapes, however, are provided by way of example only and not limitation. Expansion of the area 410 increases a size and/or dimension of the area 410 to enable the introduction of a device. At the same time, expansion of the scaffold 400 may generally reduce a cross sectional area of the body 402 because of the elastic deformation.

In an alternative embodiment, a non-elastic material may be used that is configured such that the overall structure has a tendency to recover substantially to a pre-expansion profile. For example, a coiled band of non-elastic material, such as a coil spring, may nonetheless be expanded during insertion of a device through a central opening, and yet it will recover substantially to the initial profile when the device is removed even though the entire structure may not have undergone an elastic expansion in the traditional sense. This discussion underscores the broad use of the term elastic in this description. That is, elastic may refer to an elastic material in the traditional sense, e.g. that the material may be deformed and thereafter recover substantially to its initial configuration, as well as the use in which a material that is pliable or flexible may be used to create a scaffold 110 that has an area which may expand and contract in response to the insertion of an object therethrough.

The body 402 includes an interior portion 408 and an exterior portion 406. The body 400 can be tubular in shape, but may have other configurations including a configuration where one side is substantially flat. For example, the portion of the body in contact with or adjacent the vessel wall may be flat. The interior area 410 is typically defined by at least the interior portion 408 of the body 402. The scaffold 400 can be deformed such that dimensions or shape of the interior area 410 can be changed. The elasticity of the material used in the body 402 enables the change in shape to occur in multiple directions. for instance, the insertion of an oval shaped device expands the scaffold 400 more in one direction than in another directions. Changing the dimensions of the interior area 410 enables medical devices of different sizes to be accommodated in the interior area 410 defined by the scaffold 400 as previously stated.

The elasticity of the body 402 allows the scaffold 400 to be expanded to an expanded position (e.g., to accommodate the introduction and/or removal of various medical devices). When the device is withdrawn or the expanding force is removed, the resiliency of at least the body 402 of the scaffold 400 returns the scaffold 400 to the closed position.

FIG. 4 shows that one or more anchors 404 extend from the body 402 of the scaffold 400. The anchors 404 are configured to embed in and/or pierce the vessel's wall proximate the opening in the vessel. As the body 402 expands (e.g., because of the introduction of a device), the anchors 404 may distribute the force to a wider area of the vessel rather than just to the opening. For example, the force associated with the insertion of a device is often directed directly to the tissue around the opening in the vessel. The scaffold 400 can distribute this force to a wider area. In other words, the area inside the boundaries of the scaffold 400 is at least partially protected from trauma by the scaffold 400. As a result, the trauma to the vessel at the opening, or more generally to the puncture site, can be reduced or minimized.

Figure 5:
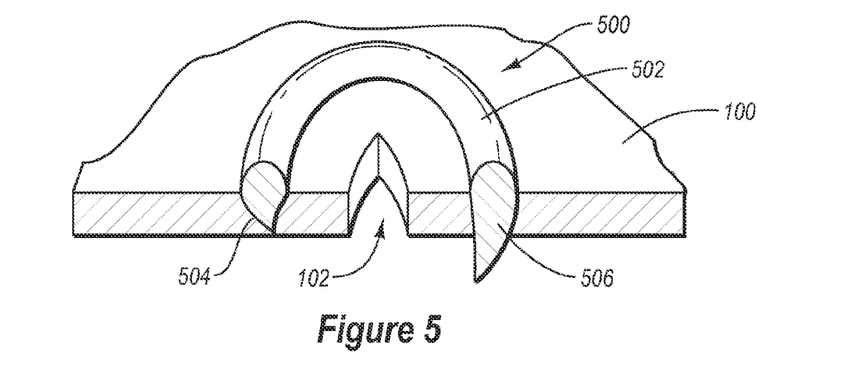
FIG. 5 shows an illustrative example of engagement mechanisms that attach the scaffold to the tissue.
Figure 6:
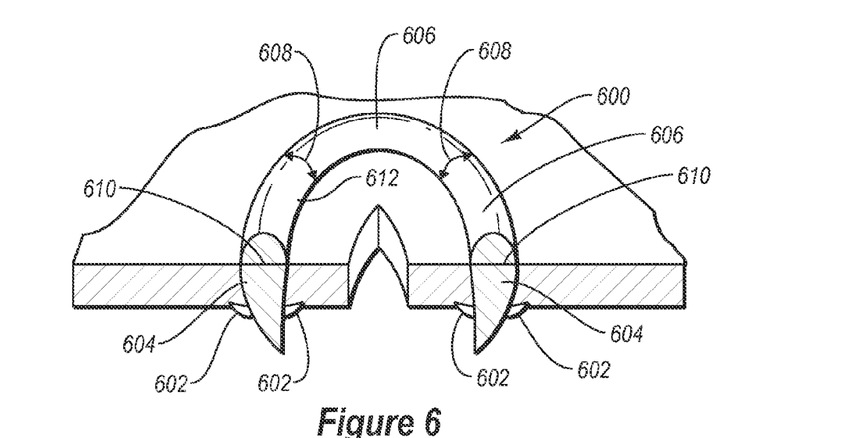
FIG. 6 shows another illustrative example of engagement mechanisms for attaching a scaffold to the tissue.

The anchors 404 can extend from the inner portion 408 and/or the outer portion 406, and/or a bottom portion 412 of the body 402. The anchors 404 may be curved and may extend orthogonally from the body 402 or at an angle relative to the body 402. For example, the anchors 404 may each curve inwardly toward the opening in the vessel. The anchors 404 may also be curved away from the opening in the vessel. Once anchored, the scaffold 400 is less likely to become displaced during use when the anchors are curved. The anchors 404 typically narrow to a point 414 capable of penetrating tissue FIGS. 5 and 6 illustrate variations, by way of example and not limitation, in the shape and/or dimension of the anchors 404. FIG. 5 illustrates another example of a scaffold 500, which is an example of the scaffold 110. More specifically, the scaffold 500 illustrates variations in the configuration of the anchors and/or of the body of the scaffold 500. The scaffold 500 includes an anchor 504 that is shaped to only partially penetrate a wall of the vessel 100. The scaffold 500 also illustrate that the anchor 506 is configured to completely pierce the vessel wall 100.

As illustrated in FIG. 5, the scaffold 500 is placed proximate the opening 102 and the anchors 504/506 curve inwardly toward the opening 102 in this example. In some examples, the scaffold 500 can include anchors having different characteristics. The scaffold 500 may include short anchors, relatively longer anchors, anchors that are oriented in different directions or that curve in different directions, anchors with different dimensions (e.g., thickness, length, radius of curvature, etc.) and the like or any combination thereof.

FIG. 6 shows another example of a scaffold 600, which is an example of the scaffold 110. In this example, the scaffold 600 includes anchors 604. Barbs 602 are formed on the anchors 604. The barbs 602 are angled to enable insertion of the scaffold 600 into the tissue proximate the opening. Once the scaffold 600 is engaged with the tissue, the barbs 602 may ensure that the scaffold 600 remains anchored with the tissue as the scaffold expands and/or contracts to accept or accommodate the insertion/removal of medical devices.

As the scaffold 600 expands and/or contracts, a body 606, like a body of other embodiments of the scaffold disclosed herein, may rotate in the directions of the arrows 608. For instance, the insertion of a medical device may engage an inner portion 612 of the body 606, causing the body 606 to rotate inwardly when expanding. Removal of the device may cause the body 606 to rotate outwardly when contracting. The anchors 604 and/or the barbs 602 keep the scaffold 600 connected with the tissue during a procedure and can reduce or minimize rotation of the body 606. In another example, the rotation of the scaffold 600 may be minimal during insertion/removal of a medical device.

Alternatively, the body 606 may be formed from or coated with a smooth or slippery (e.g., low coefficient of friction) material such that rotation of the body 606 is reduced. In an embodiment, the smooth material may be a hydrophilic or hydrophobic surface coating. This may reduce the rotation that the scaffold 600 may otherwise experience when formed of a material that is non-slip.

Figure 7:
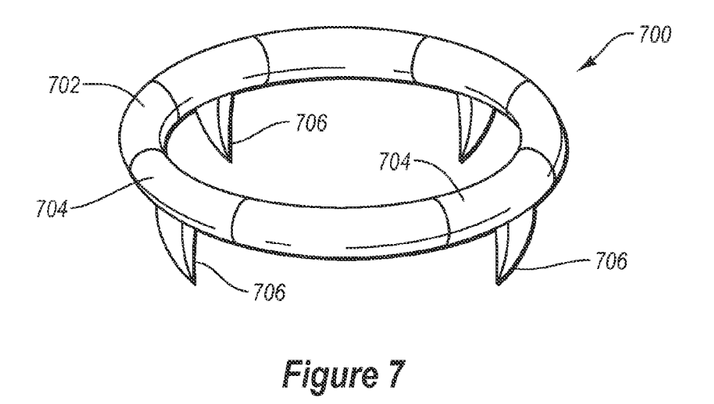
FIG. 7 shows a perspective view of another embodiment of an anchor for managing access to tissue.

FIG. 7 illustrates another example of a scaffold 700, which is an example of the scaffold 110. FIG. 7 illustrate a segmented scaffold 700 The segmented scaffold 700 illustrates that the segments included in the scaffold may have different elasticities and/or resiliencies. The scaffold 700, for example, enables segments associated with anchors to be less elastic than neighboring segments. During a procedure, the elasticity is therefore borne by the more elastic segments. At the same time, the anchors may be less subject to becoming displaced, for example, by movement of the inserted device.

The scaffold 700 includes segments 702 and 704 that are joined together in a circular arrangement, although embodiments of the scaffolds disclosed herein can be arranged in other geometric configurations (e.g., ellipse or multi-sided configurations). In addition, the segments 702 and 704 are generally tubular, but may have other configurations including a flat portion as previously described. The segments 704 are typically formed of a more rigid, non-elastic or less elastic material (although this material may be flexible and may have shape memory) than the segments 702, which are typically formed of flexible and/or elastic material.

The segments 704, by being less elastic than the segments 702, each have a length that provides support to the scaffold 700 and can help keep the scaffold 700 engaged with the tissue during the insertion/removal of a medical device through the scaffold 700. The segments 704, for instance can aid in reducing rotation of the body of the scaffold 700, provide structural support to the body of the scaffold 700, or the like. Expansion/contraction of the scaffold 700 is achieved by the elasticity/resiliency of the sections 702.

The scaffold 700 includes anchors 706. The anchors 706 may be formed integrally with the segments 704 or may be attached to the segments 704. This configuration allows the elastic segments 702 to expand while keeping the scaffold 700 engaged with the tissue. In other words, the anchors 706 are more likely to remain engaged with the tissue because the corresponding segments 704 are less elastic than the sections 702 or non-elastic.

The flexibility and/or elasticity of the segments 702 also allows the segments 704 to adapt to changes in orientation and/or movement of medical devices during a procedure. In one example, the elasticity of the segments 702 enables the scaffold 700 to expand and contract to allow the introduction/removal of medical devices while providing tissue support. In addition, the rigidity of the segments 704 ensure that the anchors 706 do not become dislodged due to expansion/contraction. In other words, the expandability of the scaffold 700 is primarily located in the segments 702, allowing the segments 704 to anchor the scaffold 700 to the tissue. In other embodiments, the anchors 706 can be integrally formed with or connected to the segments 704 and/or the segments 702. In addition, the segments 702 and 704 can each be associated with more than one anchor.

The segments 704 may also be flexible without being elastic. This allows the segments 704 to adapt to changes in orientation of the scaffold 700. The elasticity is provided by the segments 702.

In another example, the segments 704 and 702 represent portions of the scaffold 700 that have been treated differently to alter characteristics of the scaffold 700. For instance, the segments 702 may be treated chemically and/or thermally to alter a stiffness or elasticity of the segment 702. As a result, the body of the scaffold 700 can be formed from the same material and then treated in specific locations to induce different characteristics in the segments 720 and 704.

Figure 8A:
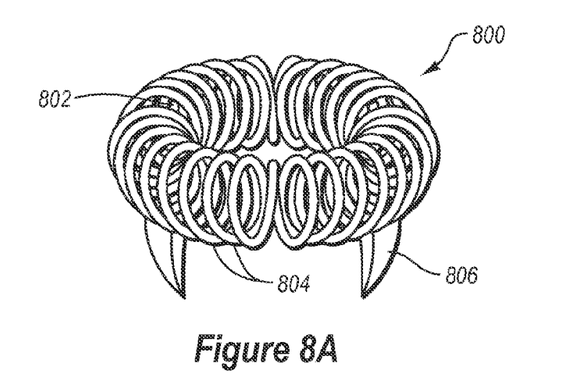
FIGS. 8A and 8B show an illustrative example of a scaffold.
Figure 8B:
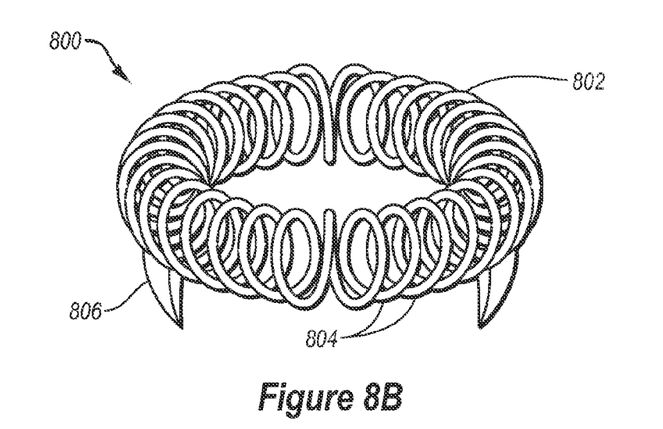

FIG. 8A illustrates another embodiment of a scaffold 800 in a contracted position. FIG. 8B illustrates the scaffold 800 in an expanded position. The scaffold 800 includes a body 802 that may be a coiled spring having individual coils 804. FIG. 8A shows the body in a contracted position where the coils 804 are at rest. Insertion of a medical device expands the body 802 as shown in FIG. 8B such that the individual coils of the body 802 are spaced. Anchors 806 can be attached to one or more individual coils of the body 802. In one example, the coils attached to the anchors 806 may have less expansion than coils that are not attached to the anchors 806.

Figure 9:
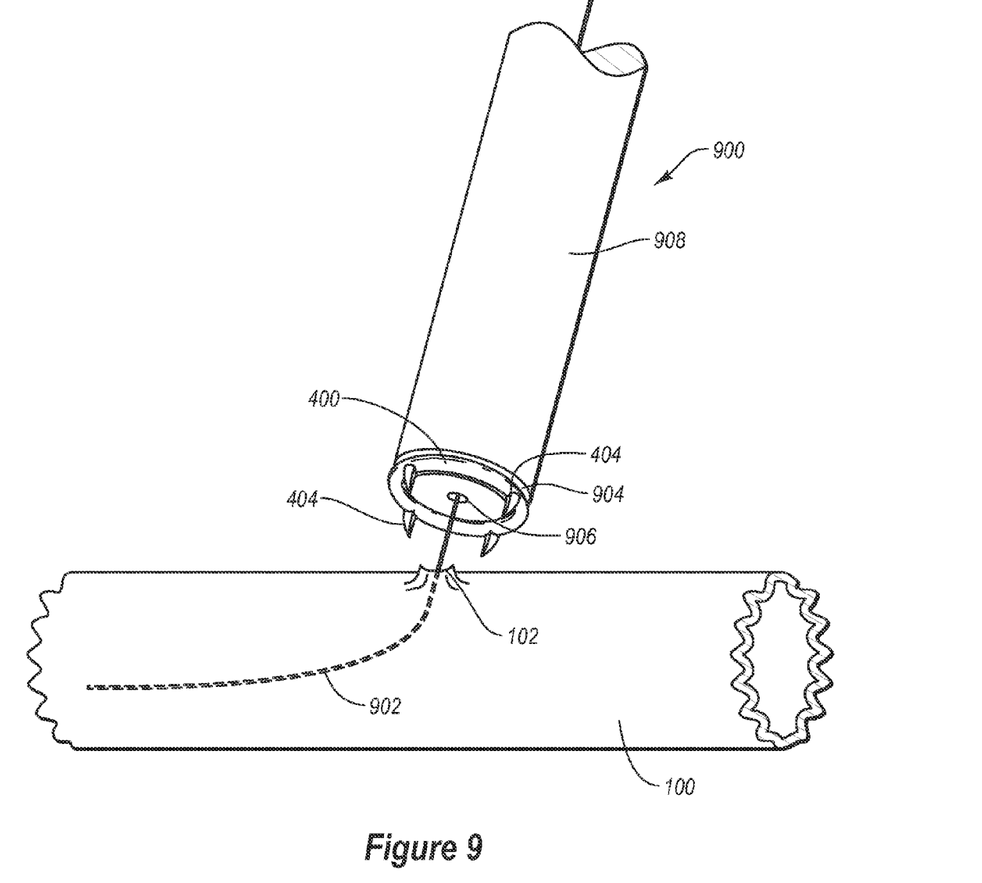
FIG. 9 shows an illustrative example of a delivery device for deploying a scaffold.

FIG. 9 illustrates an example of a delivery device deploying a scaffold, such as the scaffold 400 illustrated in FIG. 4.

The scaffold 400 may be delivered to the opening 102 (e.g., an arteriotomy) in a number of ways and using a number of different device configurations. In an embodiment, after creating the opening 102 with an access needle in the vessel 100 and then accessing the vessel with a guidewire 902 that is delivered through the needle lumen, the needle may be removed. A delivery device 900 may then be tracked over the guidewire to the arteriotomy site. The delivery device 900 may have a cylindrical body 908 with an inner lumen 906 closely conforming to the diameter of the guidewire 902 and an outer diameter that is greater than the profile of the opening 102. This ensures that the body 908 can track over the guidewire 902, but will not easily pass into the body vessel 100. Furthermore, the scaffold 400 may be associated with a distal end 904 of the body 908 such that the anchors 404 of the scaffold 400 project toward the vessel 100 as the scaffold 400 is delivered over the guidewire 902 by the delivery device 900. Thus, when the body 908, which may be cylindrical, is advanced toward the opening 102, the body 908 will sandwich the scaffold 600 between the body vessel tissue and a distal end 904 of the body 908. This sandwiching will provide the force required for the anchors 404 to puncture and embed within the body vessel tissue. In one example, the distal end 904 of the delivery device 900 may have a recess configured to accommodate the scaffold 400. The recess may be able to retain the scaffold 400 until the anchors 404 engage the tissue of the vessel 100 around the opening 102.

Other delivery system embodiments may be used in accordance with the teaching of this invention. For example, the scaffold 400 may be flexible enough to be positioned within the barrel of a delivery system similar to the Starclose device manufactured by Abbott Vascular in Redwood City, Calif. Such an embodiment would allow the operator to track the scaffold 400 over a guidewire and to position it accurately against the arteriotomy using the placement features of the Starclose device. Additionally, a delivery device such as this would allow the operator to affirmatively control the deployment of the scaffold 400 using deployment features such as buttons, levers, triggers, etc. that would actuate the delivery device to deploy the scaffold 400 into the body vessel tissue.

The scaffold may comprise various elastic, flexible, and pliable materials. For example, at least one portion of the scaffold may be formed from a material such as silicone or various types of thermoplastic elastomers (TPEs). Alternatively, at least one portion of the scaffold may be formed from a material such as polyamides, polyurethanes, silicone modified polyurethanes, fluoropolymers, polyolefins, polyimides, polyimines, (methyl)acrylic polymers, polyesters, polyglycolide, polyglycolide (PGA), poly(L-lactide) (PLLA), poly (D,L-lactide) (PDLLA), poly(L-lactide-co-glycolide) (PLGA), poly(D,L-lactide-co-glycolide) (PDLGA), poly(e-caprolactone) (PCL), polydioxanone, poly(ethylene glycol) (PEG), poly(vinyl alcohol), and co-polymers thereof. It will be appreciated that the scaffold may also comprise at least one portion formed from a deformable such as stainless steel, platinum, tantalum, palladium, and/or cobalt-chromium alloys, or shape memory metals such as nickel-titanium alloys.

In one embodiment, the scaffold can include a variety of suitable deformable alloy metal materials, including stainless steel, silver, platinum, tantalum, palladium, cobalt-chromium alloys or other known biocompatible alloy metal materials. In an alternative embodiment, the scaffold can include a variety of suitable shape memory metal materials such as nickel-titanium alloys.

In one embodiment, the scaffold can include a suitable biocompatible polymer in addition to or in place of a suitable metal. The scaffold can include biodegradable or bioabsorbable materials, which can be elastically deformable.

It is further contemplated that the external surface and/or internal surface of the scaffold or scaffold element (e.g., exterior and/or luminal surfaces) can be coated with another material having a composition different from a primary scaffold material. The use of a different material to coat the surfaces can be beneficial for imparting additional properties to the clip, such as providing radiopaque characteristics, drug-reservoirs, and improved biocompatibility.

In one configuration, the external and/or internal surfaces of a scaffold can be coated with a biocompatible polymeric material as described herein. Such coatings can include hydrogels, hydrophilic and/or hydrophobic compounds, and polypeptides, proteins or amino acids or the like. Specific examples can include polyethylene glycols, polyvinylpyrrolidone (PVP), polyvinylalcohol (PVA), parylene, heparin, phosphorylcholine, polytetrafluorethylene (PTFE), or the like.

Accordingly, the coating material can contain a drug or beneficial agent to improve the use of the scaffold. Such drugs or beneficial agents can include antibiotics, for example.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A scaffold for managing access to an opening in tissue, the scaffold comprising:
   an annular, planar body having an outer surface, the body including a material configured to expand between a first position and a second position, the body defining a longitudinal central axis through an opening in the body, the body having a first diameter and a second diameter, the first diameter being orthogonal to the second diameter, the first diameter and the second diameter both reducing in size between the second position and the first position; and
   at least one anchor extending from the outer surface toward the longitudinal central axis and configured to engage the tissue proximate the opening, the annular body being without protrusions extending toward the longitudinal central axis from the body other than the at least one anchor such that the body comprises a smooth substantially annular shape configured to reduce friction between the inner portion and a medical device inserted through the interior area of the body.

2. The scaffold of claim 1, wherein the body comprises an inner portion defining a boundary around the opening, wherein the material comprises a material capable of expanding to an expanded position and toggled to recover toward the first position and to a third position.

3. The scaffold of claim 1, wherein the body deforms when expanding from the first position to the second position such that a cross sectional area of the body measured through the body and parallel to the longitudinal central axis decreases.

4. The scaffold of claim 1, wherein the at least one anchor comprises one or more barbs to engage the tissue, wherein the one or more barbs are angled to facilitate insertion of the one or more anchors in the tissue while resisting removal of the one or more anchors from the tissue.

5. The scaffold of claim 1, wherein the at least one anchor curves inwardly toward the opening when engaged with the tissue.

6. The scaffold of claim 1, wherein the at least one anchor is curved in at least one direction.

7. The scaffold of claim 6, wherein the body is substantially annular without protrusions extending toward the longitudinal central axis from the body other than the at least one anchor such that the body comprises a smooth substantially annular shape configured to prevent rotation of the body during insertion and removal of a medical device from the opening.

8. The scaffold of claim 1, wherein the body comprises first segments and second segments, wherein the first segments are formed from an elastic material and the second segments are formed from a less-elastic material, wherein the at least one anchor extend from the second segments.

9. The scaffold of claim 1, wherein portions of the material are treated at least one of chemically and thermally such that the body includes first segments having an elasticity that is different from an elasticity of second segments.

10. The scaffold of claim 1, wherein the at least one anchor does not include any barbs.

11. The scaffold of claim 1, wherein the material of the body is biodegradable and elastically deformable.

12. The scaffold of claim 1, wherein the material of the body is an elastically deformable plastic.

13. The scaffold of claim 1, wherein the material of the body is a shape memory plastic.

14. The scaffold of claim 1, wherein the one or more anchors comprise four anchors.

15. A scaffold for controlling trauma to an opening in tissue, the scaffold comprising:
   an annular, planar body having an inner portion and an outer portion, the inner portion defining an interior area, wherein the body comprises a cross sectional area measured through the body and parallel to the longitudinal central axis that reduces when the body expands from a first position to a second position and wherein the body comprises a material that expands from a first position to a second expanded position and that contracts toward the first position from the second expanded position to a third position, the body defining an annular shape having a longitudinal central axis through the opening in the body that is perpendicular to a plane extending through the entire body; and
   one or more anchors extending from the body toward the longitudinal central axis in both the first position and the second expanded position, the one or more anchors narrowing to a point and configured to engage the tissue proximate the opening.

16. The scaffold of claim 15, wherein the body comprises a flat area perpendicular to the longitudinal central axis configured to be positioned adjacent the tissue proximate the opening.

17. The scaffold of claim 15, wherein the material dynamically deforms in response to changes in an orientation of a medical device inserted through the interior area of the body.

18. The scaffold of claim 15, wherein the one or more anchors curve inwardly towards the interior area.

19. The scaffold of claim 15, wherein at least some of the one or more anchors have a curved shape.

20. The scaffold of claim 15, wherein the one or more anchors comprise barbs extending from sides of the one or more anchors, wherein the barbs facilitate insertion of the one or more anchors into the tissue and resist removal of the one or more anchors from the tissue.

21. The scaffold of claim 15, wherein the body comprises first segments and second segments, wherein the first segments include the material and the second segments comprise a less elastic material.

22. The scaffold of claim 21, wherein the one or more anchors are tissue penetrating and extend from the second segments.

23. The scaffold of claim 15, wherein the body is substantially annular without protrusions extending toward the longitudinal central axis from the body other than the at least one anchor such that the body comprises a smooth substantially annular shape configured to reduce friction between the inner portion and a medical device inserted through the interior area of the body.

24. The scaffold of claim 15, wherein the one or more anchors are integrally formed with the body.

25. The scaffold of claim 15, wherein the one or more anchors comprise a second material that is non-elastic.

26. The scaffold of claim 15, wherein the body is configured to absorb forces exerted on the tissue by a medical device inserted through the interior area and through the opening.

27. The scaffold of claim 15, wherein the material of the body is biodegradable and elastically deformable.

28. The scaffold of claim 15, wherein the material of the body is an elastically deformable plastic.

29. The scaffold of claim 15, wherein the material of the body is a shape memory plastic.

30. The scaffold of claim 15, wherein the one or more anchors do not include any barbs.

31. The scaffold of claim 15, wherein the body has a first diameter and a second diameter, the first diameter being orthogonal to the second diameter, the first diameter and the second diameter both reducing in size between the first position and the second position.

32. A scaffold for managing access to an opening in tissue, the scaffold comprising:

an annular, planar body having an outer surface, the body including a shape memory plastic material configured to expand between a first position and a second position, the body defining a longitudinal central axis through an opening in the body that is perpendicular to a plane extending through the entire body, the body including a cross sectional area measured through the body and parallel to the longitudinal central axis that reduces when the body expands from a first position to a second position, the body having a first diameter and a second diameter, the first diameter being orthogonal to the second diameter, the first diameter and the second diameter both reducing in size between the second position and the first position; and six anchors extending from the outer surface toward the longitudinal central axis and configured to engage the tissue proximate the opening, the annular body being without protrusions extending toward the longitudinal central axis from the body other than the at least one anchor such that the body comprises a smooth substantially annular shape configured to reduce friction between the inner portion and a medical device inserted through the interior area of the body.

* * * * *